United States Patent
Prokhorov

(10) Patent No.: US 9,776,042 B2
(45) Date of Patent: Oct. 3, 2017

(54) EXERCISE SYSTEM AND METHOD FOR CONTROLLING A VEHICLE

(71) Applicant: TOYOTA MOTOR ENGINEERING & MANUFACTURING NORTH AMERICA, INC., Erlanger, KY (US)

(72) Inventor: Danil V. Prokhorov, Canton, MI (US)

(73) Assignee: TOYOTA MOTOR ENGINEERING & MANUFACTURING NORTH AMERICA, INC., Erlanger, KY (US)

( * ) Notice: Subject to any disclaimer, the term of this patent is extended or adjusted under 35 U.S.C. 154(b) by 51 days.

(21) Appl. No.: 15/044,447

(22) Filed: Feb. 16, 2016

(65) Prior Publication Data

US 2017/0232297 A1 Aug. 17, 2017

(51) Int. Cl.
*A63B 24/00* (2006.01)
*G09B 5/06* (2006.01)
*A63B 22/06* (2006.01)
*A63B 22/00* (2006.01)
(Continued)

(52) U.S. Cl.
CPC ...... *A63B 24/0062* (2013.01); *A63B 22/0025* (2015.10); *A63B 22/0076* (2013.01); *A63B 22/0605* (2013.01); *A63B 23/0205* (2013.01); *A63B 23/03516* (2013.01); *A63B 24/0003* (2013.01); *A63B 24/0075* (2013.01); *G09B 5/06* (2013.01); *A63B 2022/0033* (2013.01); *A63B 2022/0035* (2013.01)

(58) Field of Classification Search
CPC ............ A63B 24/0062; A63B 22/0076; A63B 24/0003; A63B 22/0605; A63B 24/0075; A63B 22/0025; A63B 23/0205; A63B 23/03516; A63B 2022/0035; A63B 2022/0033; G09B 5/06
See application file for complete search history.

(56) References Cited

U.S. PATENT DOCUMENTS

| 4,013,287 A | 3/1977 | Dickman |
| 5,036,937 A | 8/1991 | Tanaka |
| 5,141,482 A | 8/1992 | Hern |

(Continued)

FOREIGN PATENT DOCUMENTS

| JP | 9-254698 A | 9/1997 |
| JP | 2000211573 A * | 8/2000 |

(Continued)

*Primary Examiner* — Darlene P Condra
(74) *Attorney, Agent, or Firm* — Oblon, McClelland, Maier & Neustadt, L.L.P.

(57) ABSTRACT

A vehicular exercise system includes an exercise monitoring apparatus configured to communicate with a vehicle including one or more internal structures including at least one seat and a steering wheel. The at least one exercise monitoring apparatus includes processing circuitry configured to detect one or more exercise activities performed at the one or more internal structures and actuate the vehicle based on the one or more detected exercise activities. The processing circuitry is further configured to monitor one or more physiological parameters of the one or more detected exercise activities, determine a recommendation regarding future exercise activities based on the one or more physiological parameters, and output one or more notifications corresponding to the one or more physiological parameters and the determined recommendation.

20 Claims, 7 Drawing Sheets

(51) Int. Cl.
   *A63B 23/02*    (2006.01)
   *A63B 23/035*   (2006.01)

(56) References Cited

U.S. PATENT DOCUMENTS

| | | | | |
|---|---|---|---|---|
| 5,242,181 | A | 9/1993 | Fales et al. | |
| 5,769,085 | A * | 6/1998 | Kawakami | A61B 5/024 600/519 |
| 5,890,995 | A * | 4/1999 | Bobick | A63B 22/16 434/247 |
| 7,229,392 | B2 * | 6/2007 | Turnbull | A63B 21/04 482/129 |
| 8,593,288 | B2 * | 11/2013 | Schmitz | B60K 28/066 340/438 |
| 8,712,724 | B2 * | 4/2014 | Yuen | A61B 5/0002 702/160 |
| 2004/0144585 | A1 | 7/2004 | Vasser | |
| 2007/0085297 | A1 | 4/2007 | Eugene Cruft | |
| 2009/0181826 | A1 * | 7/2009 | Turner | A63B 24/0062 482/4 |
| 2009/0212524 | A1 | 8/2009 | Lee | |
| 2009/0233769 | A1 * | 9/2009 | Pryor | B60K 35/00 482/8 |
| 2010/0219955 | A1 | 9/2010 | Demirdjian et al. | |
| 2011/0082009 | A1 * | 4/2011 | Ranky | A63B 22/0605 482/8 |
| 2014/0210179 | A1 * | 7/2014 | Sprague | B62M 1/36 280/261 |
| 2014/0316305 | A1 * | 10/2014 | Venkatraman | A61B 5/1112 600/595 |
| 2015/0238800 | A1 | 8/2015 | Henry | |
| 2015/0329173 | A1 * | 11/2015 | de Winter | B62M 6/60 180/206.7 |
| 2015/0367176 | A1 * | 12/2015 | Bejestan | G06F 19/3481 482/9 |
| 2016/0144240 | A1 * | 5/2016 | Watterson | A63B 24/0087 482/5 |
| 2016/0150978 | A1 * | 6/2016 | Yuen | A61B 5/0205 600/301 |
| 2016/0185418 | A1 * | 6/2016 | Stegmaier | B62M 6/45 701/22 |

FOREIGN PATENT DOCUMENTS

| | | |
|---|---|---|
| JP | 2007-202597 A | 8/2007 |
| JP | 2008-213802 A | 9/2008 |

* cited by examiner

FIG. 3 Exercise Activity Detection and Response Process 300

EXERCISE SYSTEM AND METHOD FOR CONTROLLING A VEHICLE

BACKGROUND

The "background" description provided herein is for the purpose of generally presenting the context of the disclosure. Work of the presently named inventor, to the extent it is described in this background section, as well as aspects of the description which may not otherwise qualify as prior art at the time of filing, are neither expressly nor impliedly admitted as prior art against the present disclosure.

Drivers of vehicles who experience drowsiness, boredom and sedentary conditions can be dangerous on the road. These drivers pose a hazard to others as their attention is not focused on driving a vehicle. Such conditions also create issues for the drivers themselves as these conditions negatively affect the health of the drivers. It is preferential to promote the health and safety of drivers and as well as the safety of others on the road.

Currently, there are systems located inside of vehicles that promote exercise activity of the drivers. For example, in the U.S. Pat. No. 8,098,165 B2, the system addresses the drowsiness of drivers when on the road. In another example, in the U.S. Pat. No. 7,982,620 B2, the system addresses the boredom that drivers may experience when on the road. It would be beneficial for the driver to be able to exercise while continuing to operate the vehicle they are located in.

Interactive drowsiness monitoring systems exist in vehicles that seek to notify the driver when they are experiencing exhaustion or tiredness. These systems monitor the position of the driver and determine when the driver is losing focus on the operation of the vehicle. The drowsiness monitoring systems address the fatigue of drivers and actively seek to reduce such fatigue. However, the drowsiness monitoring systems do not enable the user to effectively operate the vehicle while performing acts of drowsiness-reduction.

SUMMARY

In an exemplary aspect, a vehicular exercise system includes an exercise monitoring apparatus configured to communicate with a vehicle including one or more internal structures including at least one seat and a steering wheel. The at least one exercise monitoring apparatus includes processing circuitry configured to detect one or more exercise activities performed at the one or more internal structures and actuate the vehicle based on the one or more detected exercise activities. The processing circuitry is further configured to monitor one or more physiological parameters of the one or more detected exercise activities, determine a recommendation regarding future exercise activities based on the one or more physiological parameters, and output one or more notifications corresponding to the one or more physiological parameters and the determined recommendation.

The foregoing general description of exemplary implementations and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
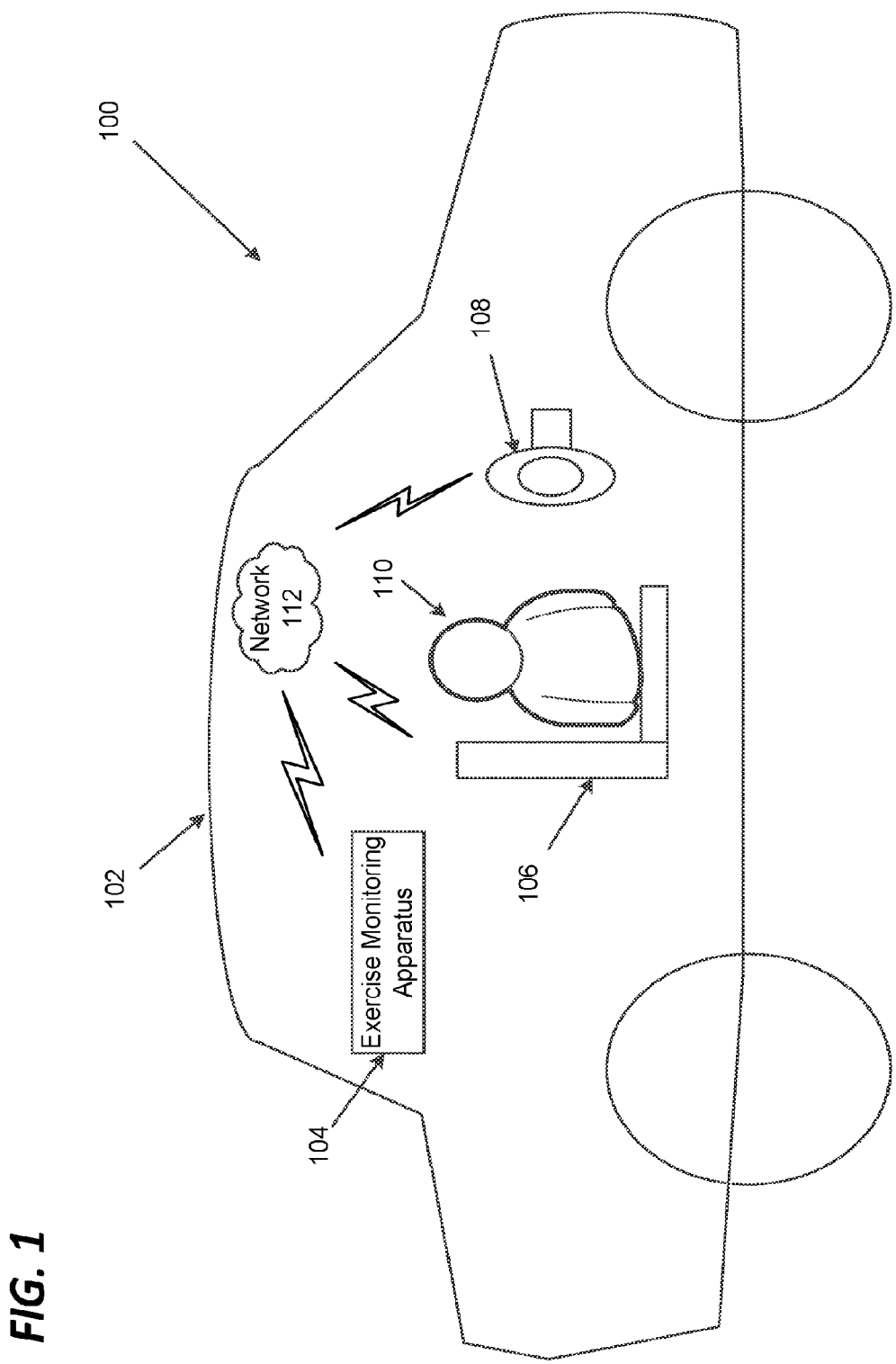
FIG. 1 is an exemplary illustration of an exercise system for controlling a vehicle, according to certain aspects.

In the drawings, like reference numerals designate identical or corresponding parts throughout the several views. Further, as used herein, the words "a," "an" and the like generally carry a meaning of "one or more," unless stated otherwise.

FIG. 1 is an exemplary illustration of an exercise system for controlling a vehicle 100, according to certain aspects of the disclosure. The exercise system for controlling a vehicle 100 includes a vehicle 102, an exercise monitoring apparatus 104 and a network 112. The exercise system for controlling a vehicle 100 is configured to detect exercise activities performed in a vehicle 102, actuate the vehicle 102 based on the exercise activities, monitor physiological parameters of a user 110 performing the exercise activities, and provide recommendations of exercise activities based on the physiological parameters.

The vehicle 102 is in communication with the exercise monitoring apparatus 104 via the network 112 and includes a seat 106, a steering wheel 108 and a user 110. The vehicle 102 can include an automobile, a truck, a van, a sport utility vehicle and the like. The vehicle 102 can be controlled by processing circuitry of the exercise monitoring apparatus 104. In certain aspects of the present disclosure, the vehicle 102 can be controlled by the circuitry of the exercise monitoring apparatus 104 via the network 112 in combination with manual user 110 controls. In other aspects, the vehicle 102 can be configured to be autonomous and receive actuation commands from the exercise monitoring apparatus 104 via the network 112.

The exercise monitoring apparatus 104 is in communication with the vehicle 102 via the network 112. The exercise monitoring apparatus 104 includes processing circuitry configured to detect exercise activities and actuate the vehicle 102 based on the exercise activities. The exercise monitoring apparatus 104 can include memory configured to store training examples of the exercise activities. The training examples can be accessed by the processing circuitry of the exercise monitoring apparatus 104 to aid the circuitry in the detection of the exercise activity being performed. The circuitry of the exercise monitoring apparatus 104 can be configured to compare movements of the user 110 with training examples of exercise activities stored on the memory. The exercise activities can be performed by the user 110. The user 110 can interact with the seat 106 and the steering wheel 108 of the vehicle 102 to perform the exercise activities. The exercise activities can include biking, rowing, pulling legs up, motion of turning the steering wheel 108 back and forth, straining abdominal muscles, pull ups, running and the like. The processes of exercise activity detection and exercise activity determination will be discussed further herein.

The circuitry of the exercise monitoring apparatus 104 can further be configured to monitor physiological parameters of the user 110 performing the exercise activities and provide recommendations of exercise activities based on the physiological parameters. The physiological parameters can include heart rate, blood pressure, respiratory rate and the like. The circuitry of the exercise monitoring apparatus 104 compares the monitored physiological parameter with a predetermined threshold. The circuitry can include a threshold value for each of the physiological parameters. The threshold can be a lower limit, an upper limit and/or a range depending on the corresponding physiological parameter. Further, each physiological parameter can correspond to more than one threshold. For example, the heart rate physiological parameter may have a first threshold indicative of an upper limit of the heart rate and a second threshold indicative of a lower limit of the heart rate. The thresholds may be determined based upon when the corresponding physiological parameter may indicate an abnormal condition, a fatal condition, an emergency situation and the like.

The circuitry can further be configured to output notifications corresponding to the physiological parameters as well as the recommendations of the exercise activities. The notifications can be output by the circuitry visually, via a graphical display in communication with the exercise monitoring apparatus 104, audibly, via a loudspeaker in communication with the exercise monitoring apparatus 104, or both. The circuitry can further be configured to recommend an exercise activity for the user 110 to perform. The recommended exercise activity can be an exercise activity that is stored in the memory of the exercise monitoring apparatus 104. The recommendation can also include recommending that the user 110 stop performing any exercise activity.

In certain aspects of the present disclosure, the exercise monitoring apparatus 104 includes a plurality of actuators that can actuate at least one of steering control, acceleration control and deceleration control of the vehicle based on the one or more exercise activities. The plurality of actuators can actuate the controls of the vehicle 102 which supplement autonomous functionalities of the vehicle such as cruise control, automated steering and the like. For example, the vehicle 102 can be set to autonomous cruise control in which the vehicle 102 maintains an average distance behind a leading vehicle while maintaining a constant average speed. The plurality of actuators can include a speed control actuator that corresponds to the speed control in which a user 110 can interact with internal structures of the vehicle 102 through an exercise activity to cause the vehicle 102 to accelerate and/or decelerate based on the intensity of the exercise activity. The vehicle control and actuation via the circuitry of the exercise monitoring apparatus 104 will be discussed further herein.

The seat 106 is located in the vehicle 102 and can be utilized in different modes to aid the user 110 in performing the exercise activities. As such, the seat 106 can be set in a static mode, a spring loaded mode, and the like. The modes of the seat 106 can aid the user in performing different exercise activities to actuate the vehicle 102 via the exercise monitoring apparatus 104. For example, the seat 106 can be set to the spring loaded mode to allow the user 110 to move in a vertical direction perpendicular to the floor of the vehicle 102 to perform the exercise activity of pull ups while remaining in contact with the seat 106. In another example, the seat 106 can be set to the spring loaded mode to allow the user 110 to move in a longitudinal direction parallel with the floor of the vehicle 102 to perform the exercise activity of rowing while remaining in contact with the seat 106.

The steering wheel 108 is located in the vehicle 102 and can be utilized in different modes to aid the user in performing the exercise activities. As such, the steering wheel 108 can be set in a static mode, a spring loaded mode, and the like. The modes of the steering wheel can aid the user in performing different exercise activities to actuate the vehicle 102 via the exercise monitoring apparatus. For example, the steering wheel 108 can be set to a spring loaded mode to allow the user to move in a longitudinal direction of the steering wheel 108 to perform the exercise activity of rowing while remaining in contact with both the steering wheel 108 and the seat 106.

The network 112 represents one or more networks 112, and is connected to the vehicle 102 and the exercise monitoring apparatus 104. The network 112 can communicate via wired networks such as Ethernet, LAN or any other wired form of communication that is known. The network 112 can also communicate via wireless networks such as Wi-Fi, Bluetooth, cellular networks including EDGE, 3G and 4G wireless cellular systems, Infrared or any other wireless form of communication that is known.

Figure 2:
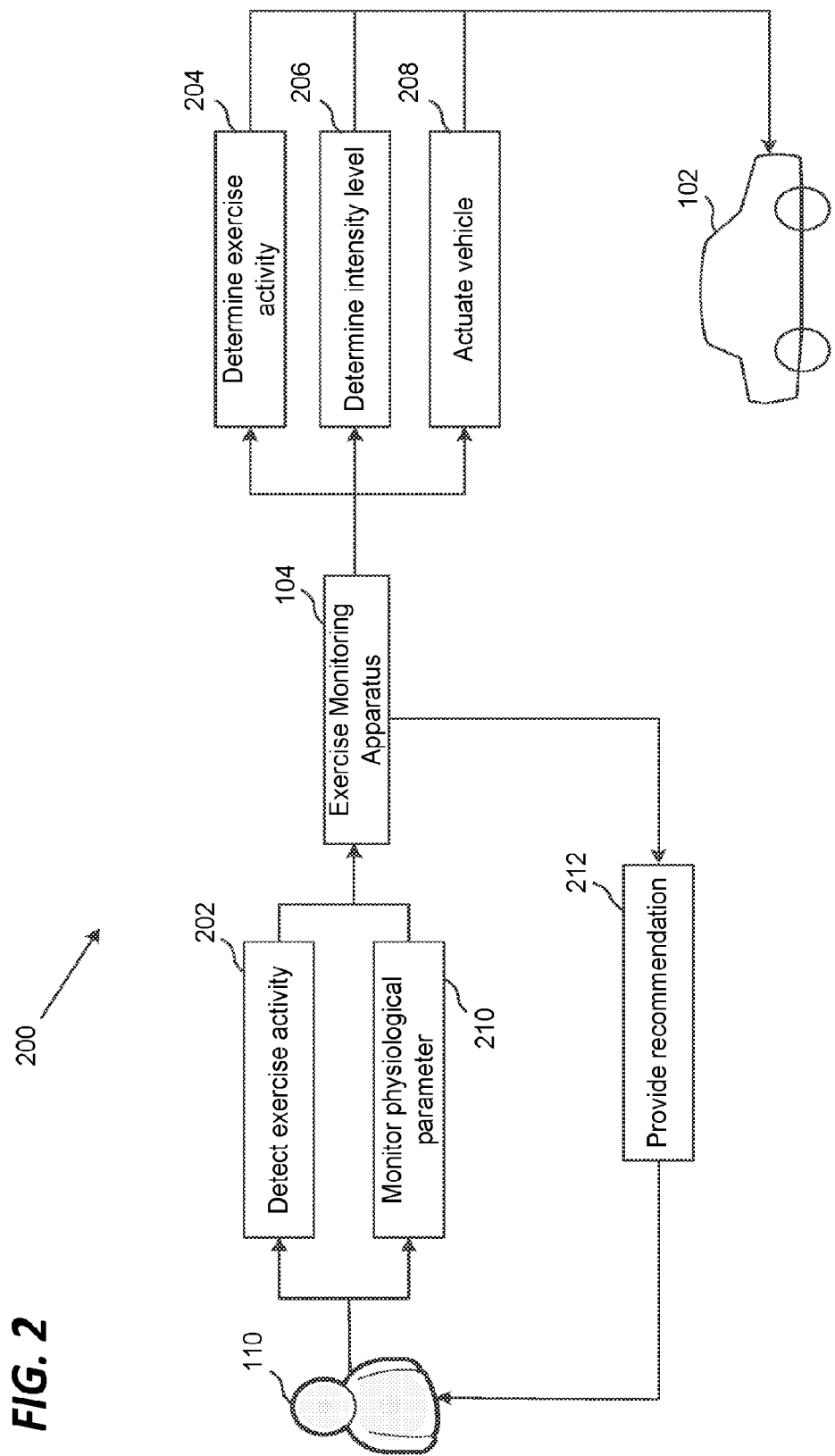
FIG. 2 is an exemplary illustration of an exercise system data workflow, according to certain aspects.

FIG. 2 is an exemplary illustration of an exercise system data workflow 200, according to certain aspects of the present disclosure. The exercise system data workflow 200 describes the acquisition of exercise activity data, the utilization of the exercise activity data to actuate the vehicle 102, the monitoring of physiological parameters and the output of exercise activity recommendations based on the physiological parameters. The user 110 performs an exercise activity that can be detected 202 by the circuitry of the exercise monitoring apparatus 104. The exercise activity can be performed by the user 110 utilizing the seat 106 and the steering wheel 108. The seat 106 and the steering wheel 108 can be set in modes such as static, spring loaded and the like. The circuitry of the exercise monitoring apparatus 104 detects the presence of the exercise activity 202 and determines the exercise activity being performed 204. The circuitry can detect the exercise activity 202 via interactions with internal structures of the vehicle 102. The internal circuitry can include a plurality of actuators configured to actuate at least one of steering control, acceleration control and deceleration control of the vehicle 102 based on the one or more detected exercise activities 202. The circuitry of the exercise monitoring apparatus 104 can obtain data corresponding to the exercise activity and compare the data with training examples of the exercise activities. The training examples can be stored in memory of the exercise monitoring apparatus 104 and accessed when exercise activity is detected.

The circuitry of the exercise monitoring apparatus 104 can be configured to determine the intensity level 206 of the exercise activity being performed. The intensity level of the exercise activity 206 can be utilized to actuate 208 the vehicle 102 at a predetermined rate. For example, the exercise activity of rowing can be performed by the user 110 to increase the acceleration of the vehicle 102. The intensity of rowing of the user 110 can correspond to a rowing rate in which the user 110 physically actuates the steering wheel 108 in the longitudinal direction and/or the seat 106 in the longitudinal direction. The rowing rate of the user 110 can correspond to the rate at which the acceleration of the vehicle 102 is increased. As such, the circuitry can be configured to monitor the rowing rate of the user 110 when the exercise activity of running is performed by the user 110. The circuitry can utilize the determined rowing rate to increase the acceleration of the vehicle 102 to a predetermined value corresponding to the rowing rate.

In another example, the exercise activity of pull ups can be performed by the user 110 to decelerate the vehicle 102. In this instance, the length of time the user 110 is performing the exercise activity of pull ups can be measured. In some aspects, the circuitry can determine the exercise activity of pull ups based on the vertical movement of the seat 108 when it is fixed in a spring loaded mode. In other aspects, the circuitry can determine the exercise activity of pull ups based on the vertical movement of the user 100 when the seat 108 is in a static mode. As such, the circuitry can be configured to continually decelerate the vehicle 102 until the user 110 is detected to no longer be performing the exercise activity of pull ups, or until the vehicle 102 has decelerated to a complete stop. In certain aspects, a single exercise activity can be performed at the internal structures of the vehicle 102 to accelerate the vehicle 102 based on a predetermined high intensity and decelerate the vehicle 102 based on a predetermined low intensity of the single exercise activity.

The circuitry of the exercise monitoring apparatus 104 can monitor physiological parameters 210 of the user 110 performing the exercise activity. The physiological parameters can include a heart rate, a blood pressure, a respiratory rate and the like. In certain aspects of the present disclosure, the circuitry monitors multiple physiological parameters 210 automatically when an exercise activity is detected. In other aspects, the circuitry monitors physiological parameters 210 when the user 110 prompts the circuitry to measure one or more physiological parameters. The circuitry can monitor the physiological parameters 212 via one or more physical contact sensors located in the seat, the steering wheel and/or a wearable device. For example, the circuitry can detect the heart rate of a user 110 of the vehicle 102 continuously via physical contact sensors located at the steering wheel. In certain aspects of the present disclosure, the circuitry monitors the physiological parameters 212 via physical contact sensors at the steering wheel and transmits notifications to a wearable device in the form of audio feedback and/or haptic feedback based on the physiological parameters. In another example, the circuitry can monitor physiological parameters at the wearable device via physical contact sensors located at the wearable device.

Based on the measured physiological parameter 210, the circuitry can provide a recommendation 212 of an exercise activity. The recommended exercise activity 212 can be provided with the intention of preventing the user 110 from over exercising, experiencing exhaustion and the like. Additionally, the recommended exercise activity 212 can seek to promote awareness of the user if the measure physiological parameter is determined to be lower than a predetermined threshold of an acceptable physiological parameter value. The circuitry can further be configured to output notifications corresponding to the physiological parameters as well as the recommendations of the exercise activities 212. The notifications can be output by the circuitry visually, via a graphical display in communication with the exercise monitoring apparatus 104, audibly, via a loudspeaker in communication with the exercise monitoring apparatus 104, or both.

Figure 3:
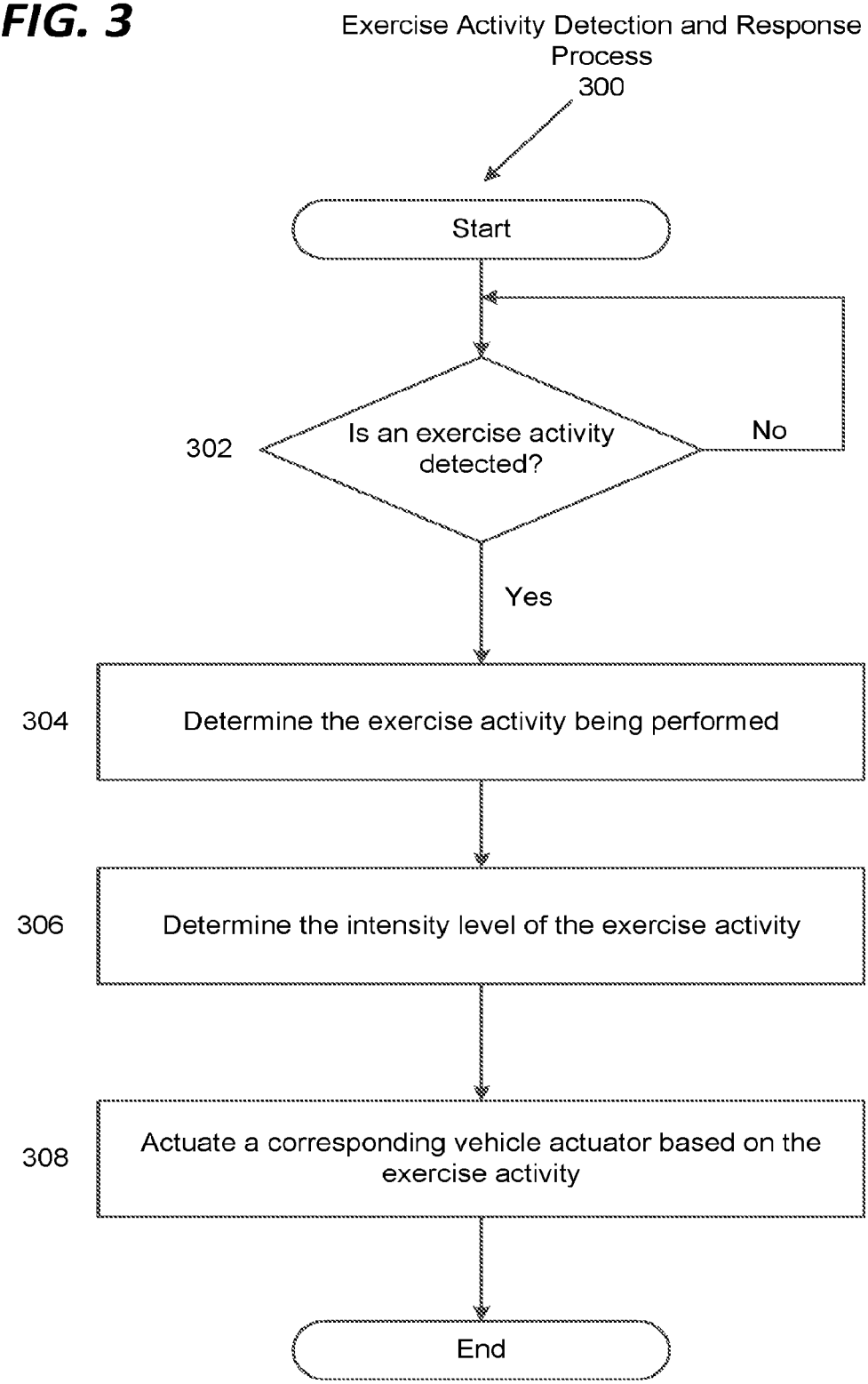
FIG. 3 is an algorithmic flowchart of an exercise activity detection and response process, according to certain aspects.

FIG. 3 is an algorithmic flowchart of an exercise activity detection and response process 300, according to certain aspects of the present disclosure. The exercise activity detection and response process 300 describes the process by which the circuitry of the exercise monitoring apparatus 104 monitors an exercise activity being performed and actuates a vehicle 102 based on the exercise activity. At step 302, a determination is made of whether an exercise activity is detected by the circuitry. The circuitry can be configured to detect the exercise activity via physical interactions with the internal structures of the vehicle 102, such as a seat 106 and/or a steering wheel 108. If an exercise activity is detected by the circuitry, resulting in a "yes" at step 302, then the exercise activity detection and response process 300 proceeds to step 304. If an exercise activity is not detected by the circuitry, resulting in a "no" at step 302, then the exercise activity detection and response process repeats step 302.

At step 304, the circuitry of the exercise monitoring apparatus 104 determines which exercise activity is being performed. The circuitry can determine the exercise activity 204 via interactions with the internal structures of the vehicle 102. For example, the exercise activity of rowing can be performed by the user 110. The rowing of the user 110 can correspond to physically actuating the steering wheel 108 in the longitudinal direction and/or the seat 106 in the longitudinal direction. The circuitry of the exercise monitoring apparatus 104 can be configured to obtain data corresponding to the exercise activity and compare the data with training examples of the exercise activities. The training examples can be stored in memory of the exercise monitoring apparatus 104 and accessed for comparison when exercise activity is detected.

At step 306, the circuitry determines the intensity level of the exercise activity being performed by the user 110. In an example, the exercise activity of rowing can be performed by the user 110 to increase the acceleration of the vehicle 102. The intensity of rowing can correspond to a rowing rate at which the user 110 physically actuates the steering wheel 108 in the longitudinal direction and/or the seat 106 in the longitudinal direction. The rowing rate of the user 110 can correspond to the rate at which the acceleration of the vehicle 102 is increased. As such, the circuitry can be configured to monitor the rowing rate of the user 110 when the exercise activity of rowing is performed by the user 110. The circuitry can utilize the determined rowing rate to increase the acceleration of the vehicle 102 to a predetermined value.

At step 308, the circuitry actuates the vehicle 102 based on the intensity of the exercise activity. The intensity level of the exercise activity can be utilized to actuate the vehicle 102 at a predetermined rate for the length of time that the user 110 is performing the exercise activity. In the example of rowing, the rowing rate of the user 110 can correspond to the rate at which the acceleration of the vehicle 102 is increased. In some aspects, the circuitry can utilize the determined rowing rate to increase the acceleration of the vehicle 102 to a predetermined value corresponding to an arm swing rate. The arm swing rate can correspond to the rate at which the user 110 of the vehicle 102 is swinging their arms while performing the exercise activity of rowing. In other aspects, the circuitry can utilize the determined rowing rate to increase the acceleration of the vehicle 102 to a predetermined value corresponding to a leg extension or contraction rate. The leg extension or contraction rate can correspond to the rate at which the user 110 of the vehicle 102 is extending or contracting their legs while performing the exercise activity of rowing. In another example, the vehicle 102 can be set to autonomous cruise control in which the vehicle 102 is configured to maintain an average distance behind a leading vehicle in addition to maintain a constant average speed. The plurality of actuators can include a speed control actuator that corresponds to the speed control in which a user 110 can interact with internal structures of the vehicle 102 through an exercise activity to cause the vehicle 102 to accelerate or decelerate based on the intensity of the exercise activity. In certain aspects, a single exercise activity can be performed at the internal structures of the vehicle 102 to accelerate the vehicle 102 based on a predetermined high intensity and decelerate the vehicle 102 based on a predetermined low intensity of the single exercise activity. In other aspects, a single exercise activity can be performed at the internal structures of the vehicle 102 to accelerate the vehicle 102 based on a predetermined low intensity and decelerate the vehicle 102 based on a predetermined high intensity of the single exercise activity.

Figure 4:
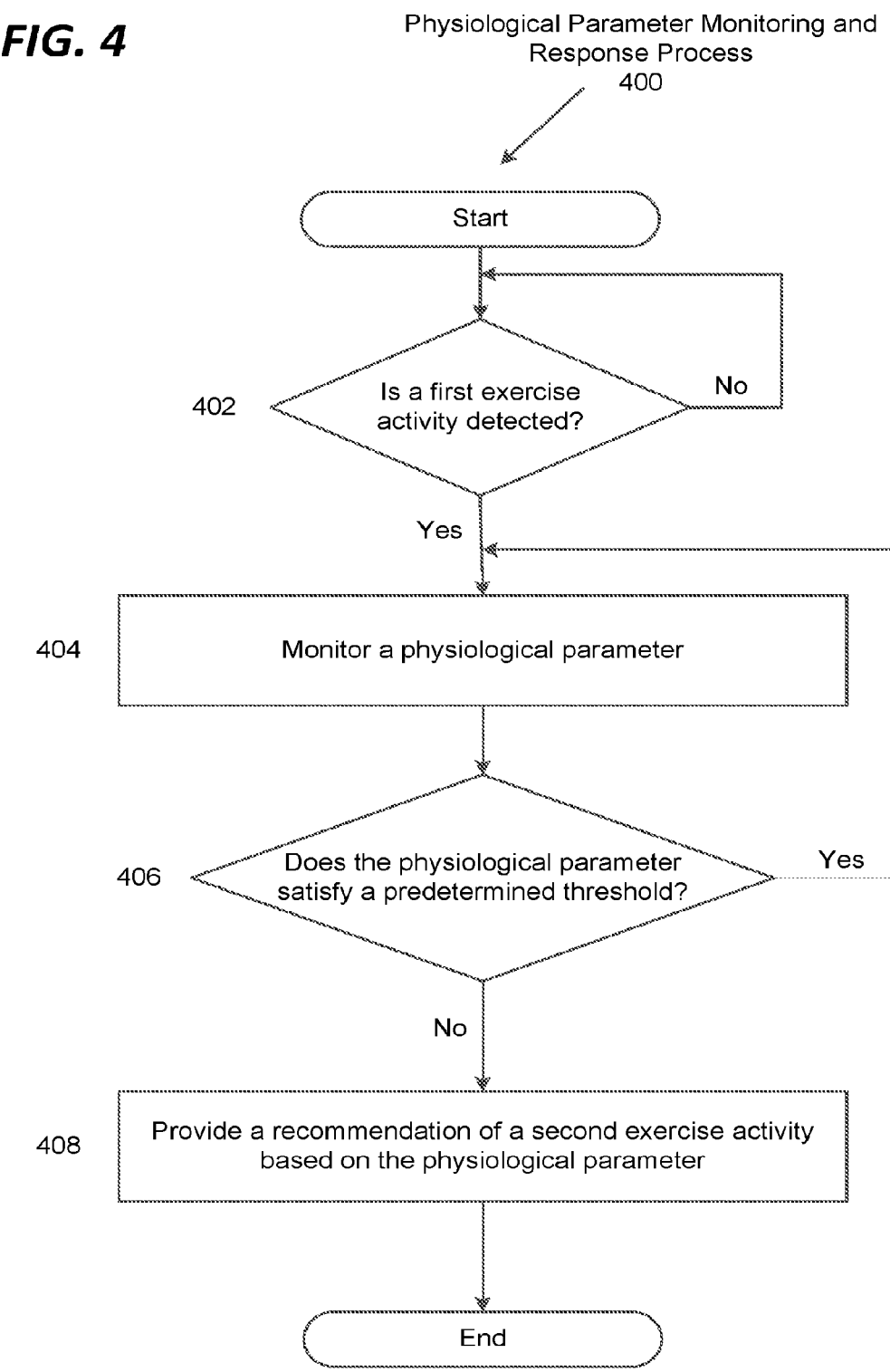
FIG. 4 is an algorithmic flowchart of a physiological parameter monitoring and response process, according to certain aspects.

FIG. 4 is an algorithmic flowchart of a physiological parameter monitoring and response process 400, according to certain aspects of the present disclosure. The physiological parameter monitoring and response process 400 describes the process in which the circuitry of the exercise monitoring apparatus 104 monitors physiological parameters of a user 110 performing an exercise activity and provides a recommendation of an exercise activity based on the monitored physiological parameters. At step 402, a determination is made of whether an exercise activity is detected by the circuitry. The circuitry can detect the exercise activity via physical interactions with the internal structures of the vehicle 102, such as a seat 106 and/or a steering wheel 108. If an exercise activity is detected by the circuitry, resulting in a "yes" at step 402, then the physiological parameter monitoring and response process 400 proceeds to step 404. If an exercise activity is not detected by the circuitry, resulting in a "no" at step 402, then the physiological parameter monitoring and response process 400 repeats step 402.

At step 404, the circuitry of the exercise monitoring apparatus 104 can monitor physiological parameters of the user 110 performing the exercise activity. The physiological parameters can include a heart rate, a blood pressure, a respiratory rate and the like. In certain aspects of the present disclosure, the circuitry monitors multiple physiological parameters automatically when an exercise activity is detected. In other aspects, the circuitry monitors physiological parameters when the user 110 prompts the circuitry to measure one or more physiological parameters. The circuitry can monitor the physiological parameters via one or more physical contact sensors located in the seat, the steering wheel and/or a wearable device.

At step 406, a determination is made of whether the physiological parameter satisfies a predetermined threshold. The circuitry of the exercise monitoring apparatus 104 compares the monitored physiological parameter with a predetermined threshold. The circuitry includes a threshold value for each of the physiological parameters. The threshold can be a lower limit, an upper limit and/or a range depending on the corresponding physiological parameter. Further, each physiological parameter can correspond to more than one threshold. For example, the heart rate physiological parameter may have a first threshold indicative of an upper limit of the heart rate and a second threshold indicative of a lower limit of the heart rate. The thresholds may be determined based upon when the corresponding physiological parameter may indicate an abnormal condition, a fatal condition, an emergency situation and the like. If the physiological parameter satisfies the predetermined threshold, resulting in a "yes" at step 406, then the physiological parameter monitoring and response process 400 proceeds to step 404. Otherwise, if the physiological parameter does not satisfy the predetermined threshold, resulting in a "no" at step 406, then the physiological parameter monitoring and response process 400 proceeds to step 408.

At step 408, the circuitry of the exercise monitoring apparatus 104 provides a recommendation of an exercise activity based on the monitored physiological parameter. The circuitry notifies the user 110 that the monitored physiological parameter does not satisfy the predetermined threshold via a notification. The notifications can be output by the circuitry visually, via a graphical display in communication with the exercise monitoring apparatus 104, audibly, via a loudspeaker in communication with the exercise monitoring apparatus 104, or both. The circuitry can further be configured to recommend an exercise activity for the user 110 to perform. The recommended exercise activity can be an exercise activity that is stored in the memory of the exercise monitoring apparatus 104. The recommendation can also include recommending that the user 110 stop performing any exercise activity.

Figure 5:
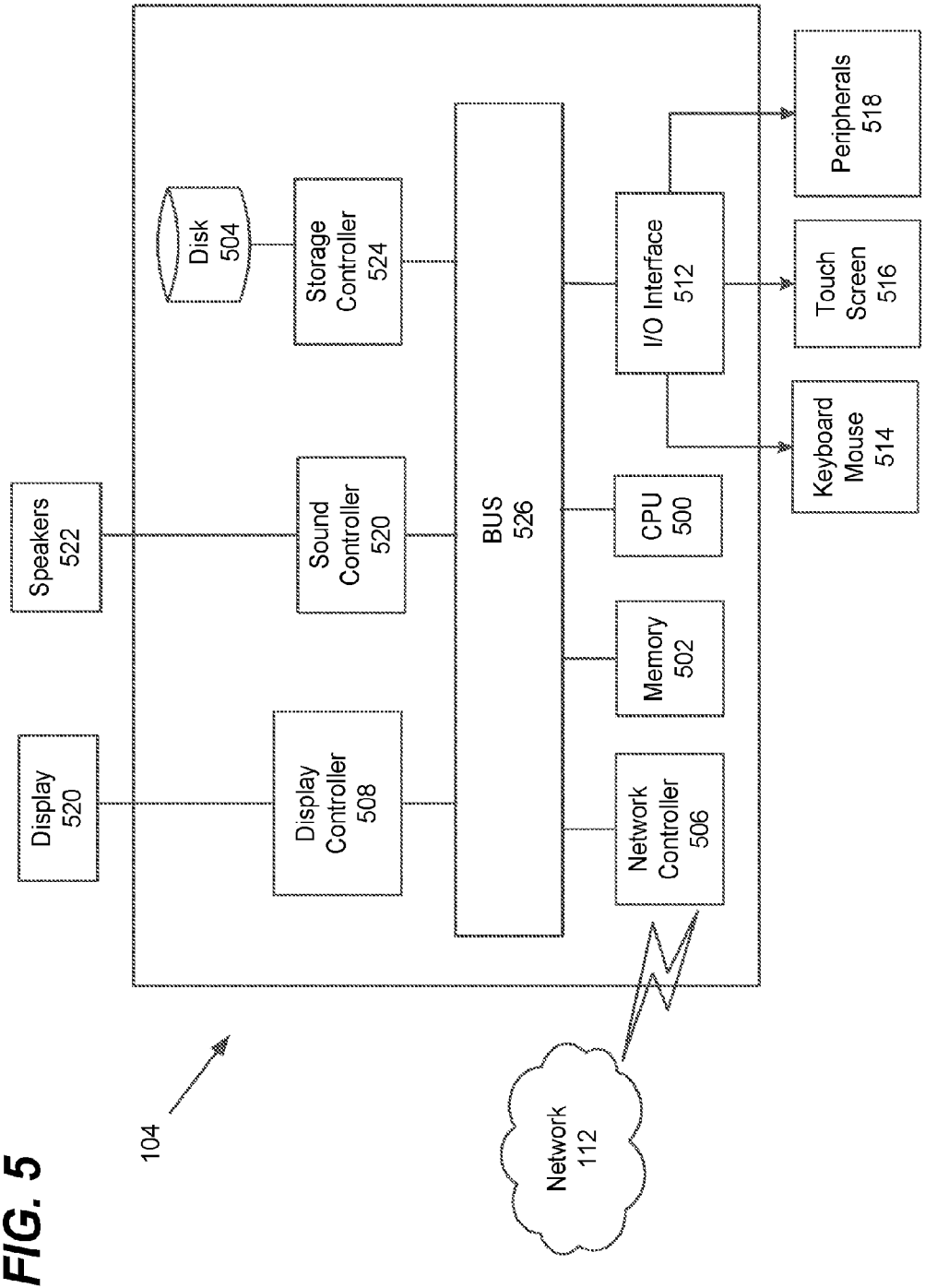
FIG. 5 illustrates a hardware block diagram of an exercise monitoring apparatus, according to certain exemplary aspects.

FIG. 5 illustrates a hardware block diagram of an exercise monitoring apparatus, according to certain exemplary aspects. In FIG. 5, the exercise monitoring apparatus 104 includes a CPU 500 which performs the processes described above/below. The process data and instructions may be stored in memory 502. These processes and instructions may also be stored on a storage medium disk 504 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the exercise monitoring apparatus 104 communicates, such as a server or computer.

Further, the claimed advancements may be provided as a utility application, background daemon, or component of an operating system, or combination thereof, executing in conjunction with CPU 500 and an operating system such as Microsoft Windows 7, UNIX, Solaris, LINUX, Apple MAC-OS and other systems known to those skilled in the art.

The hardware elements in order to achieve the exercise monitoring apparatus 104 may be realized by various circuitry elements, known to those skilled in the art. For example, CPU 500 may be a Xenon or Core processor from Intel of America or an Opteron processor from AMD of America, or may be other processor types that would be recognized by one of ordinary skill in the art. Alternatively, the CPU 500 may be implemented on an FPGA, ASIC, PLD or using discrete logic circuits, as one of ordinary skill in the art would recognize. Further, CPU 500 may be implemented as multiple processors cooperatively working in parallel to perform the instructions of the inventive processes described above.

The exercise activity apparatus in FIG. 5 also includes a network controller 506, such as an Intel Ethernet PRO network interface card from Intel Corporation of America, for interfacing with network 112. As can be appreciated, the network 112 can be a public network, such as the Internet, or a private network such as an LAN or WAN network, or any combination thereof and can also include PSTN or ISDN sub-networks. The network 112 can also be wired, such as an Ethernet network, or can be wireless such as a cellular network including EDGE, 3G and 4G wireless cellular systems. The wireless network can also be Wi-Fi, Bluetooth, or any other wireless form of communication that is known.

The exercise monitoring apparatus 104 further includes a display controller 508, such as a NVIDIA GeForce GTX or Quadro graphics adaptor from NVIDIA Corporation of America for interfacing with display 510, such as a Hewlett Packard HPL2445w LCD monitor. A general purpose I/O interface 512 interfaces with a touch screen panel 516 on or separate from display 510. General purpose I/O interface also connects to a variety of peripherals 518 including printers and scanners, such as an OfficeJet or DeskJet from Hewlett Packard.

A sound controller 520 is also provided in the exercise monitoring apparatus 104, such as Sound Blaster X-Fi Titanium from Creative, to interface with speakers/microphone 522 thereby providing sounds and/or music.

The general purpose storage controller 524 connects the storage medium disk 504 with communication bus 526, which may be an ISA, EISA, VESA, PCI, or similar, for interconnecting all of the components of the exercise monitoring apparatus 104. A description of the general features and functionality of the display 510, as well as the display controller 508, storage controller 524, network controller 506, sound controller 520, and general purpose I/O interface 512 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 6

Figure 6:
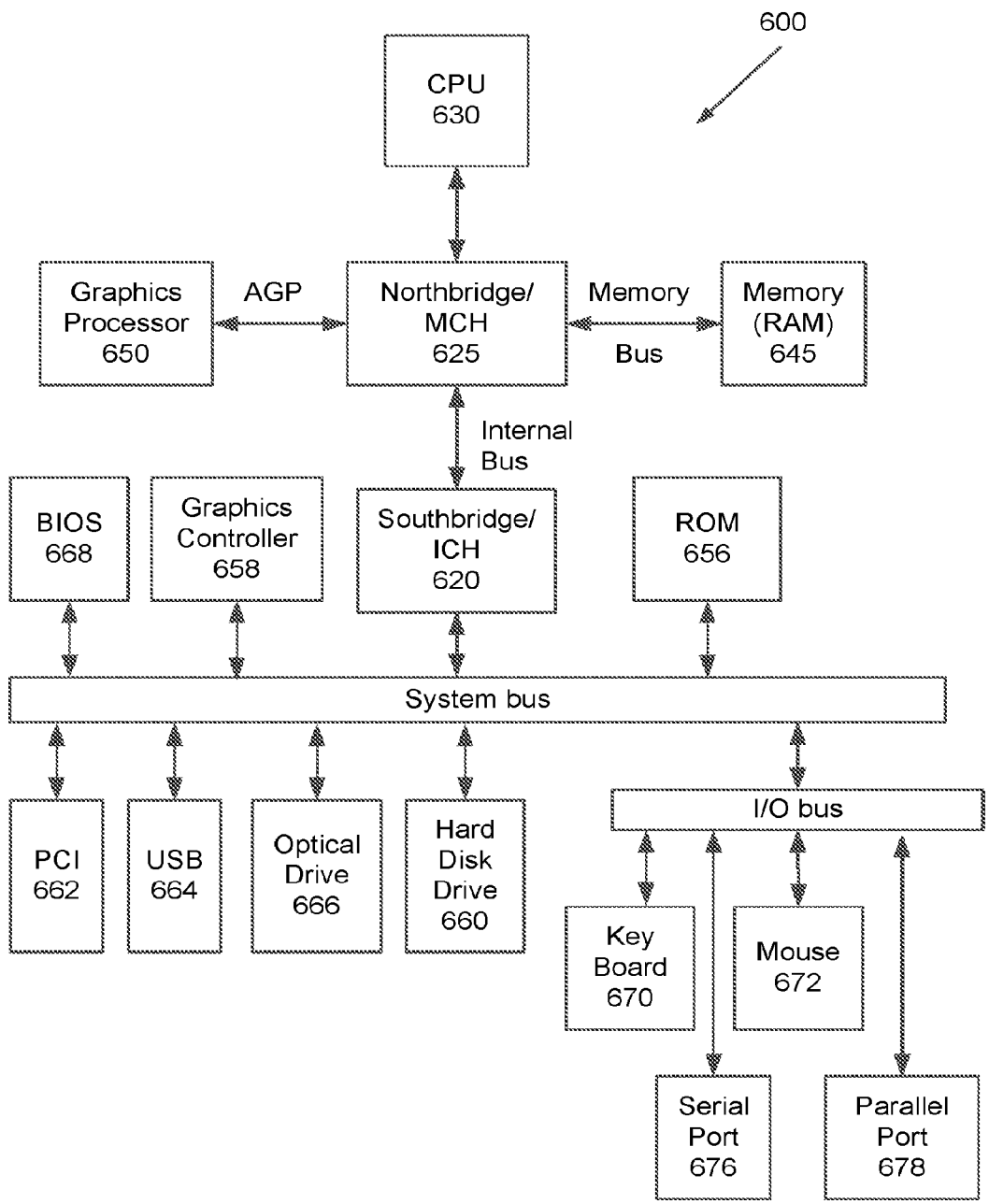
FIG. 6 illustrates a hardware block diagram of a data processing system, according to certain exemplary aspects.

FIG. 6 illustrates a hardware block diagram of a data processing system 600, according to certain exemplary aspects of the present disclosure. The data processing system is an example of a computer in which code or instructions implementing the processes of the illustrative aspects may be located.

In FIG. 6, data processing system 600 employs a hub architecture including a north bridge and memory controller hub (NB/MCH) 625 and a south bridge and input/output (I/O) controller hub (SB/ICH) 620. The central processing unit (CPU) 630 is connected to NB/MCH 625. The NB/MCH 625 also connects to the memory 645 via a memory bus, and connects to the graphics processor 650 via an accelerated graphics port (AGP). The NB/MCH 625 also connects to the SB/ICH 620 via an internal bus (e.g., a unified media interface or a direct media interface). The CPU Processing unit 630 may contain one or more processors and even may be implemented using one or more heterogeneous processor systems.

Figure 7:
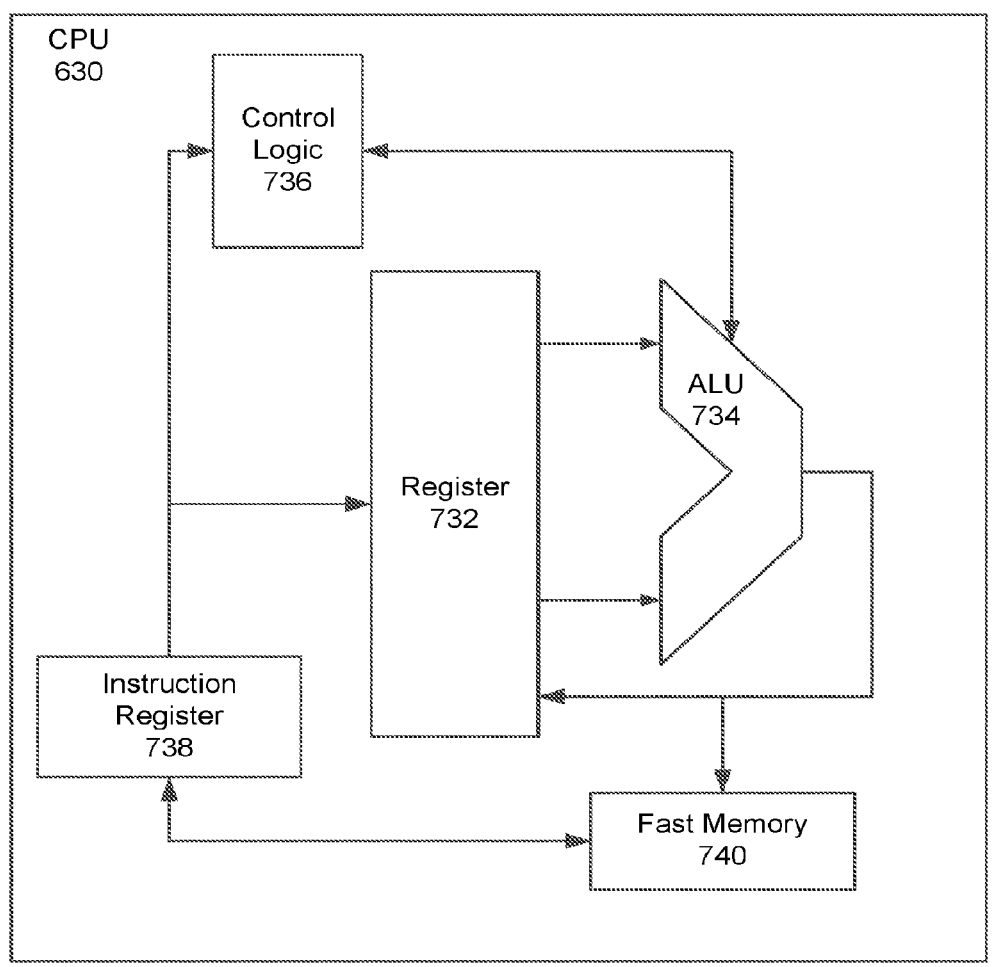
FIG. 7 illustrates a hardware block diagram of a CPU, according to certain exemplary aspects.

FIG. 7 illustrates a hardware block diagram of a CPU, according to certain exemplary aspects of the present disclosure. For example, FIG. 7 shows one implementation of CPU 630. In one implementation, the instruction register 738 retrieves instructions from the fast memory 740. At least part of these instructions are fetched from the instruction register 738 by the control logic 736 and interpreted according to the instruction set architecture of the CPU 630. Part of the instructions can also be directed to the register 732. In one implementation the instructions are decoded according to a hardwired method, and in another implementation the instructions are decoded according a microprogram that translates instructions into sets of CPU configuration signals that are applied sequentially over multiple clock pulses. After fetching and decoding the instructions, the instructions are executed using the arithmetic logic unit (ALU) 734 that loads values from the register 732 and performs logical and mathematical operations on the loaded values according to the instructions. The results from these operations can be feedback into the register and/or stored in the fast memory 740. According to certain implementations, the instruction set architecture of the CPU 630 can use a reduced instruction set architecture, a complex instruction set architecture, a vector processor architecture, a very large instruction word architecture. Furthermore, the CPU 630 can be based on the Von Neuman model or the Harvard model. The CPU 630 can be a digital signal processor, an FPGA, an ASIC, a PLA, a PLD, or a CPLD. Further, the CPU 630 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 6, the data processing system 600 can include that the SB/ICH 620 is coupled through a system bus to an I/O Bus, a read only memory (ROM) 656, universal serial bus (USB) port 664, a flash binary input/output system (BIOS) 668, and a graphics controller 658. PCI/PCIe devices can also be coupled to SB/ICH YYY through a PCI bus 662.

The PCI devices may include, for example, Ethernet adapters, add-in cards, and PC cards for notebook computers. The Hard disk drive 660 and CD-ROM 666 can use, for example, an integrated drive electronics (IDE) or serial advanced technology attachment (SATA) interface. In one implementation the I/O bus can include a super I/O (SIO) device.

Further, the hard disk drive (HDD) 660 and optical drive 666 can also be coupled to the SB/ICH 620 through a system bus. In one implementation a parallel port 678 and a serial port 676 can be connected to the system bust through the I/O bus. Other peripherals and devices that can be connected to the SB/ICH 620 using a mass storage controller such as SATA or PATA, an Ethernet port, an ISA bus, a LPC bridge, SMBus, a DMA controller, and an Audio Codec.

The functions and features described herein may also be executed by various distributed components of a system. For example, one or more processors may execute these system functions, wherein the processors are distributed across multiple components communicating in a network. The distributed components may include one or more client and server machines, which may share processing, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process.

The above-described hardware description is a non-limiting example of corresponding structure for performing the functionality described herein.

A number of implementations have been described. Nevertheless, it will be understood that various modifications may be made without departing from the spirit and scope of this disclosure. For example, preferable results may be achieved if the steps of the disclosed techniques were performed in a different sequence, if components in the disclosed systems were combined in a different manner, or if the components were replaced or supplemented by other components. The functions, processes and algorithms described herein may be performed in hardware or software executed by hardware, including computer processors and/or programmable circuits configured to execute program code and/or computer instructions to execute the functions, processes and algorithms described herein. Additionally, an implementation may be performed on modules or hardware not identical to those described. Accordingly, other implementations are within the scope that may be claimed.

The invention claimed is:

1. A vehicular exercise system, comprising:
at least one exercise monitoring apparatus configured to communicate with a vehicle including one or more internal structures including at least one seat and a steering wheel, the at least one exercise monitoring apparatus including processing circuitry configured to
detect one or more exercise activities performed at the one or more internal structures,
actuate the vehicle based on the one or more detected exercise activities,
monitor one or more physiological parameters of the one or more detected exercise activities,
determine a recommendation regarding future exercise activities based on the one or more physiological parameters; and
output one or more notifications corresponding to the one or more physiological parameters and the determined recommendation.

2. The vehicular exercise system of claim 1, wherein the vehicle is an automobile, a truck, a van or a sport utility vehicle.

3. The vehicular exercise system of claim 1, wherein the one or more detected exercise activities include at least one of biking, rowing, pulling legs up, pushing the steering wheel back and forth, bending from a waist up, flexing abdominal muscles, pull ups and running.

4. The vehicular exercise system of claim 1, wherein the at least one seat and the steering wheel are configured to perform the one or more detected exercise activities in at least one of a static mode and a spring loaded mode.

5. The vehicular exercise system of claim 1, wherein the one or more physiological parameters include at least one of a heart rate, a blood pressure and a respiratory rate.

6. The vehicular exercise system of claim 1, wherein the exercise monitoring apparatus further comprises a plurality of actuators configured to actuate at least one of steering control, acceleration control and deceleration control of the vehicle based on the one or more detected exercise activities.

7. The vehicular exercise system of claim 1, wherein the circuitry is further configured to detect the one or more physiological parameters via one or more physical contact sensors located in at least one of the at least one seat, the steering wheel and at least one device wearable by the driver.

8. The vehicular exercise system of claim 1, wherein the recommended future exercise activity is a recommendation to stop or modify the one or more detected exercise activities.

9. The vehicular exercise system of claim 1, wherein the one or more notifications are output visually, via a graphical display in communication with the at least one exercise monitoring apparatus, and audibly, via a loudspeaker in communication with at least one smart menu apparatus.

10. A method of exercise monitoring in a vehicle, comprising:
detecting, via processing circuitry of at least one exercise monitoring apparatus, one or more exercise activities performed at one or more internal structures of the vehicle;
actuating, via the circuitry, the vehicle based on the one or more detected exercise activities;
monitoring, via the circuitry, one or more physiological parameters of the one or more detected exercise activities;
determining a recommendation regarding future exercise activities based on the one or more physiological parameters; and
outputting one or more notifications corresponding to the one or more physiological parameters and the determined recommendation.

11. The method of claim 10, wherein the vehicle is an automobile, a truck, a van or a sport utility vehicle.

12. The method of claim 10, wherein the one or more detected exercise activities include at least one of biking, rowing, pulling legs up, pushing a steering wheel back and forth, bending from a waist up, flexing abdominal muscles, pull ups and running.

13. The method of claim 10, wherein the vehicle includes at least one seat and steering wheel configured to perform the one or more detected exercise activities in at least one of a static mode and a spring loaded mode.

14. The method of claim 10, wherein the one or more physiological parameters include at least one of a heart rate, a blood pressure and a respiratory rate.

15. The method of claim 10, further comprising:
actuating at least one of steering control, acceleration control and deceleration control of the vehicle based on the one or more detected exercise activities.

16. The method of claim 10, further comprising:
detecting the one or more physiological parameters via one or more physical contact sensors located in at least one of the at least one seat, the steering wheel and at least one device wearable by a driver.

17. The method of claim 10, wherein the recommended future exercise activity is a recommendation to stop or modify the one or more detected exercise activities.

18. The method of claim 10, wherein the one or more notifications are output visually, via a graphical display in communication with the at least one exercise monitoring apparatus, and audibly, via a loudspeaker in communication with at least one smart menu apparatus.

19. An exercise monitoring apparatus, comprising:
processing circuitry configured to:
detect one or more exercise activities,
actuate at least one vehicle based on the one or more detected exercise activities,
monitor one or more physiological parameters of the one or more detected exercise activities,
determine a recommendation regarding future exercise activities based on the one or more physiological parameters; and
output one or more notifications corresponding to the one or more physiological parameters and the determined recommendation.

20. The exercise monitoring apparatus of claim 19, further comprising:
a plurality of actuators configured to actuate at least one of steering control, acceleration control and deceleration control of the vehicle based on the one or more detected exercise activities.

* * * * *